United States Patent [19]

Park et al.

[11] Patent Number: 5,371,274

[45] Date of Patent: Dec. 6, 1994

[54] METHODS FOR PRODUCING ETHYLIDENE DIACETATE USING CATALYSTS SUPPORTED ON AN ORGANIC CARRIER

[75] Inventors: Dae C. Park; Sung Y. Cho; Woo S. Chang, all of Deajonjikhal, Rep. of Korea

[73] Assignee: Korean Research Institute of Chemical Technology, Daejonjikhal, Rep. of Korea

[21] Appl. No.: 94,485

[22] Filed: Jul. 19, 1993

Related U.S. Application Data

[62] Division of Ser. No. 773,034, Oct. 8, 1991, abandoned.

[30] Foreign Application Priority Data

Oct. 8, 1990 [KR] Rep. of Korea ............... 1990 15918

[51] Int. Cl.$^5$ .............................................. C07C 67/36
[52] U.S. Cl. .............................................. 560/232
[58] Field of Search ............... 560/232, 263, 265, 266, 560/607, 240; 562/891; 502/150

[56] References Cited

U.S. PATENT DOCUMENTS

| | | | |
|---|---|---|---|
| 3,855,307 | 12/1974 | Rony et al. | 260/604 HF |
| 3,940,432 | 12/1976 | Walker et al. | 260/449 R |
| 4,012,450 | 3/1977 | Bond | 260/604 HF |
| 4,133,776 | 1/1979 | Pruett et al. | 252/431 N |
| 4,193,942 | 3/1980 | Gerritsen et al. | 260/604 HF |
| 4,246,183 | 1/1981 | Knifton | 260/408 |
| 4,258,206 | 3/1981 | Pittman, Jr. et al. | 560/233 |
| 4,325,834 | 4/1982 | Bartish et al. | 252/429 R |
| 4,581,473 | 4/1986 | Polichnowski | 560/263 |
| 4,665,266 | 5/1987 | Hsu et al. | 502/167 X |
| 4,667,053 | 5/1987 | Lin | 560/204 |
| 4,690,912 | 9/1987 | Paulik et al. | 502/161 |
| 4,810,821 | 3/1989 | Paulik et al. | 560/232 |
| 4,871,432 | 10/1989 | Pardy | 204/182.4 |
| 5,026,903 | 6/1991 | Baker | 560/232 |
| 5,117,046 | 5/1992 | Paulik et al. | 560/232 |

OTHER PUBLICATIONS

Rideal, Concepts in Catalysis, 1968, Pub. by Academic Press, N.Y., N.Y., pp. 4–5.
JACS 93, pp. 3062–3063, Jun. 16, 1971 (Grubbs et al.).

*Primary Examiner*—Arthur C. Prescott
*Attorney, Agent, or Firm*—Browning, Bushman, Anderson & Brookhart

[57] ABSTRACT

The present invention relates to the field of catalyst technology, and more particularly to the preparation of a supported catalyst and a method of producing ethylidene diacetate using that supported catalyst. The catalyst is represented by the formula $M_aX$. Compound M includes a group VIII transition metal which catalyzes the formation of ethylidene diacetate, preferably a compound of rhodium or palladium. Carrier X is an organic carrier, preferably selected from the divinylbenzene-polystyrene copolymers, most preferably copolymers having about 1–20% crosslinking. The weight percent of metal M contained in the catalyst is represented by the latter a. The supported heterogenized catalyst results from covalent bonding of the transition metal compound to the organic polymer carrier. Ethylidene diacetate was produced by reacting methyl acetate, iodomethane, carbon monoxide and hydrogen in the presence of this supported catalyst and an accelerator at elevated temperature and pressure. According to the present invention, the reaction product, ethylidene diacetate, is easily separated from the catalyst. The produced ethylidene diacetate may be used as a starting material for preparing vinyl acetate monomer.

10 Claims, No Drawings

METHODS FOR PRODUCING ETHYLIDENE DIACETATE USING CATALYSTS SUPPORTED ON AN ORGANIC CARRIER

This is a division of application Ser. No. 07/773,034, filed Oct. 8, 1991 now abandoned.

BACKGROUND OF THE INVENTION

1. Field of the Invention

The present invention relates to catalysts supported on organic carriers and useful for preparing ethylidene diacetate and to methods for preparing and using those catalysts in a continuous process for manufacturing ethylidene diacetate represented by the following formula:

$$CH_3CH(OCCH_3)_2 \quad (I)$$

2. Background of the Invention

Various methods for producing ethylidene diacetate are known in the art. In all of these methods ethylidene diacetate has been prepared in batch reactor systems. Because known processes for preparing ethylidene diacetate employ a homogeneous catalytic reaction, there have been no known attempts to prepare this product by a continuous process. Conventional methods for preparing ethylidene diacetate have used homogeneous catalysts, e.g., transition metals such as rhodium, ruthenium, palladium and platinum. Difficulties arose in separating these homogeneous catalysts from the reaction products.

There are few literature or patent references regarding methods for producing ethylidene diacetate. Several of these references disclose methods wherein methyl acetate, carbon monoxide and hydrogen are reacted in tile presence of a homogeneous catalyst to produce ethylidene diacetate. While these methods which employ a homogeneous catalyst produce good selectivity and yield, all suffer from several significant disadvantages, including difficulties associated with separating and purifying the reaction products from the catalyst. Conventional homogeneous catalysts employed in these methods include complexes of group VIII transition metals, preferably rhodium, ruthenium, iridium, palladium and platinum. Japanese Pat. No. 51-115409 and European Pat. No. 0028474 disclose methods for producing ethylidene diacetate using a homogeneous rhodium catalyst. Japanese Pat. No. 54-98713 and British Patent No. 1,112,555 disclose methods for producing ethylidene diacetate using homogeneous palladium catalysts. All of these methods suffer from difficulties in separating and purifying the reaction products from the homogeneous catalyst. These prior methods require the use of a distillation process to separate the homogeneous catalyst from the reaction products. For example, the '474 European patent, which discloses a method having a yield of 75.3% ethylidene diacetate based on dimethyl acetate starting material, requires a distillation step to separate the homogeneous catalyst from the reaction products.

The present invention solves the problems of the prior art by providing a novel catalyst system wherein the reaction products may be easily separated from a heterogeneous, supported catalyst. The catalyst and method of the present invention provide a simplified process for producing ethylidene diacetate and improve the productivity thereof while reducing the quantity of expensive, catalytic metal required.

By employing a catalyst supported on an organic carrier, the present invention solves tile problems in the prior art caused by the difficulties in separating prior art homogeneous catalysts from tile reaction products. The methods of the present invention simplify and improve the preparation and purification of ethylidene diacetate.

SUMMARY OF THE INVENTION

The present invention solves the problems of the prior art relating to the separation of homogeneous catalysts from reaction products by disclosing novel, heterogeneous catalysts prepared by supporting homogeneous catalyst components on organic carriers. These heterogeneous catalysts provide conversion and selectivity as good as those obtained for conventional homogeneous catalysts. Separation of the transition metal compound of the catalyst from the reaction products is simplified because the transition metal compound is believed to be covalently bonded to the organic polymer of the carrier.

The present invention is directed to a catalyst supported on an organic carrier useful for preparing ethylidene diacetate. The catalyst is represented by the following general formula:

$$M_a X \quad (II)$$

wherein M is a compound containing a group VIII transition metal which catalyzes the formation of the ethylidene diacetate. Preferably the transition metal is rhodium or palladium. More preferably compound M is selected from the group consisting of $RhCl(CO)[P(C_6H_5)_3]_2$, $RhCl(CO)[P(C_6H_5)_3]_3$, $(CH_3COO)_2Pd$ and $RhCl[P(C_6H_5)_3]_3$. X is an organic carrier preferably selected from the group consisting of the divinylbenzene-polystyrene copolymers, most preferably those having a degree of cross linking from about 1–20 percent. The weight percent of metal contained in the catalyst is represented by the subscript 'a' and preferably is from about 0.1–2.0 weight percent.

The present invention further relates to a process for preparing ethylidene diacetate using the novel, supported catalyst of formula (II) by reacting methyl acetate, iodomethane, carbon monoxide and hydrogen in the presence of the catalyst and an accelerator at a temperature between about 90°–250° C. and at a pressure between about 20–70 atmospheres.

Using the foregoing heterogeneous catalyst, separation and purification of the catalyst from the ethylidene diacetate produced in the reaction is easily accomplished. Thus, the complex separation steps, including distillation, required in prior methods using homogeneous catalysts are eliminated. Accordingly, use of the foregoing heterogeneous catalyst solves the prior art difficulties and simplifies the processes necessary for separating and purifying the produced ethylidene diacetate.

DETAILED DESCRIPTION OF THE INVENTION

The present invention provides a catalyst on an organic carrier represented by the formula $M_a X$ as defined above with formula (II). The group VIII transition metal must catalyze the production of ethylidene diacetate. Preferred transition metals include rhodium and palladium. The most preferred compounds M are selected from the group consisting of RhCl(CO)[P(C$_6$H$_5$)$_3$]$_2$, RhCl(CO)[P(C$_6$H$_5$)$_3$]$_3$, (CH$_3$COO)$_2$Pd and RhCl[P(C$_6$H$_5$)$_3$]$_3$. The most preferred transition metal compound is RhCl(CO)[P(C$_6$H$_5$)$_3$]$_3$. The organic carder X is preferably a divinylbenzene-polystyrene copolymer, most preferably having a degree of crosslinking between about 1 or 2 percent and about 20 percent.

This catalyst may be used for producing ethylidene diacetate by reacting methyl acetate, iodomethane, carbon monoxide and hydrogen in the presence of the catalyst and an accelerator. The accelerator is an organic compound containing nitrogen or phosphorous, preferably 3-picoline type compounds, most preferably triphenylphosphine.

The novel, heterogenized catalyst prepared by supporting a homogeneous catalyst on a polymeric, organic carrier provides equivalent yield and selectivity to that obtained by prior art homogeneous catalysts. However, the catalyst of the present invention offers other advantages, including simplification of the separation of the produced ethylidene diacetate from used catalyst. Such separation is achieved by simple filtration rather than more complex distillation processes required in the prior art. Another advantage of the present invention is that no acetic acid is produced as a by-product in the preparation of ethylidene diacetate. With the production of by-products inhibited and the separation of products from catalyst simplified, the distillation step required in prior art separation and purification procedures is not required.

In accord with the present invention, the heterogeneous catalyst is prepared by supporting a homogeneous catalyst on a polymeric, organic support. Divinylbenzene-polystyrene copolymers may be prepared according to any known method. These DVB-PS copolymers are then chloromethylated and phosphinated to produce the most desired catalyst support. The supported catalyst is formed by a ligard displacement reaction by contacting the group VIII transition metal compound with the resin described above.

Beginning with a gel-type divinylbenzene-polystyrene copolymer, the catalyst of the present invention supported on an organic polymeric carrier is prepared in several steps. In one preparation method, the organic polymer carrier may be prepared by reacting styrene monomer, divinylbenzene, a polymerization initiator and an emulsifier in a solvent at about 90°–100° C. and with stirring at about 250 rpm. The crosslinking degree of the organic polymer carrier is determined according to the weight ratio of divinylbenzene in the reactants. The synthesized carrier is chloromethylated at room temperature to introduce a chloromethyl (—CH$_2$Cl) group. A phosphene group is introduced to the organic carrier by addition of lithium diphenylphosphide [LiP(C$_6$H$_5$)$_2$] to the solution at room temperature. The phosphinated organic carrier is reacted with the group VIII metal compound at room temperature for about 24–72 hours to produce the supported, heterogeneous catalyst.

In the methods for producing ethylidene diacetate using the catalyst of formula (II), the following reaction conditions should be observed. The molar ratio of hydrogen to carbon monoxide feed should be from about 1:1 to about 6:1, most preferably from about 1:1 to about 3:1. The reaction temperature should be maintained between about 100°–250° C., preferably between about 130°–180° C. The concentration of catalyst should be between about 0.05–2.5 weight percent of total reactants, more preferably between about 0.1–2.0 weight percent of total reactants. The reaction time is from about 1–12 hours, preferably from about 2–6 hours. The concentration of iodomethane should be between about 10–99 weight percent of total reactants, more preferably between about 40–70 weight percent of total reactants. The reaction pressure should be between about 10–90 atmospheres, more preferably between about 20–80 atmospheres.

The yield, conversion and selectivity of the process of this invention are defined according to the following equations:

Yield(mole %) =

$$\frac{\text{(moles of ethylidene diacetate produced)}}{\text{(moles of methyl acetate feed)}} \times 100\%$$

Conversion(mole %) =

$$\frac{\text{(moles of methyl acetate reacted)}}{\text{(moles of methyl acetate feed)}} \times 100\%$$

Selectivity(mole %) =

$$\frac{\text{(moles of ethylidene diacetate produced)}}{\text{(moles of methyl acetate reacted)}} \times 100\%$$

The starting materials and products were quantitatively analyzed using gas chromatography from correlation curves obtained using anisole as the standard material to reactants and products.

The present invention will be illustrated in more detail by the following examples.

PREPARATION OF THE CATALYST

The following examples 1–12 illustrate preparation of the organic support and of catalysts in accord with the present invention.

EXAMPLE 1

A Typical Synthesis of 2% DVB-PS Resin

Polyvinylalcohol (0.11 g) and CaCO$_3$ (0.2 g, 0.89 mmole) were added to distilled water (110 ml). The reaction mixture was stirred for 30 minutes at 50° C. A solution of styrene (8.32 g, 80 mmole), divinylbenzene (1.3 g., 10 mmole) and benzoyl peroxide (0.2 g, 0.83 mmole) dissolved in xylene (16 ml) was added dropwise to the reaction mixture through a dropping funnel for 1 hour at 50° C. After the xylene had been distilled off, the reactor was cooled to room temperature and the synthesized resin washed twice using 400 ml of distilled water. The resin was washed twice again using 60 ml of 50:50 water-ethanol. Finally, the resin was washed twice again with 200 ml of methanol-dichloromethane and dried for 24 hours at room temperature in a vacuum desiccator to produce 2% DVB-PS (divinyl benzene-polystyrene) resin.

EXAMPLE 2

Chloromethylation of 2% DVB-PS Copolymer

Chloromethyl methylether (30 ml, 0.395 mole) was added to 5 g of the 2% DVB-PS copolymer produced in Example 1 and stirred for 1 hour. A solution of tin chloride (1.2 g, 0.0058 mole) dissolved in chloromethyl methylether (30 ml) was added to the reaction solution. The reaction mixture was refluxed for 1 hour, cooled to room temperature and filtered. The resin was washed with 200 ml of methanol and vacuum dried for 24 hours to produce chloromethylated 2% DVB-PS resin.

EXAMPLE 3

Phosphination of Chloromethylated 2% DVB-PS Resin

The chloromethylated copolymer produced in Example 2 (5 g) was added to 20 ml of tetrahydrofuran at room temperature under a nitrogen atmosphere. To the mixture was added 0.014 mole of $LiP(C_6H_5)_2$. The resulting mixture was stirred for 24 hours, washed with 50 ml of acetone to decompose unreacted $LiP(C_6H_5)_2$ and filtered. The resin was washed consecutively with 30 ml of acetone (again), 20 ml of water (twice), 20 ml of tetrahydrofuran (twice) and 50 ml of petroleum ether (once). The washed resin was dried at room temperature for 24 hours in a vacuum desiccator to produce phosphinated 2% DVB-PS resin.

EXAMPLE 4

Synthesis of Heterogenized Rhodium Complex

The phosphinated 2% DVB-PS resin produced in Example 3 (1.6 g) and 0.21 g (0.221 mmole) of trans $RhCl(CO)[P(C_6H_5)_3]_2$ were dissolved in 25 ml of benzene. The solution was stirred at room temperature under an atmosphere free of oxygen and moisture for 7 days until its color changed to deep scarlet. The scarlet solution was washed with 400 ml of benzene until it became colorless. The solution was dried at room temperature in a vacuum desiccator to produce the heterogenized rhodium complex catalyst.

EXAMPLE 5

The procedure of Example 1 was repeated except that the amount of divinyl benzene used was increased to 2.6 g (20 mmole). This synthesis produced a 20% DVB-PS resin.

EXAMPLE 6

The procedure of Example 2 was repeated except that 5 g of the 20% DVB-PS resin produced in Example 5 was used in place of the 2% DVB-PS resin produced in Example 1. This synthesis produced chloromethylated 20% DVB-PS resin.

EXAMPLE 7

Phosphinated 20% DVB-PS resin was prepared by repeating the procedure of Example 3 except that 5 g of the chloromethylated 20% DVB-PS resin produced in Example 6 was substituted from the chloromethylated 2% DVB-PS resin produced in Example 2.

EXAMPLE 8

A heterogenized rhodium complex catalyst was prepared by repeating the procedure of Example 4 except that 2.12 g of the phosphinated 20% DVB-PS rosin produced in Example 7 was substituted for the phosphinated 2% DVB-PS-resin produced in Example 3 and 0.20 g (0.210 mmole) of rhodium complex $RhCl(CO)[P(C_6H_5)_3]_2$ were dissolved in 25 ml of benzene.

EXAMPLE 9

A heterogenized bis-triphenylphosphine chlororhodium catalyst was prepared by following the procedure of Example 4 except that 2% DVB-PS resin prepared as in Example 3 was reacted with $RhCl[P(C_6H_5)_3]_2$.

EXAMPLE 10

A bis-triphenylphosphine chloro-rhodium catalyst was prepared by following the procedure of Example 4 except that phosphinated 20% DVB-PS resin prepared as in Example 4 was reacted with $RhCl[P(C_6H_5)_3]_2$.

EXAMPLE 11

1 g of phosphinated 2% DVB-PS resin and 0.15 g (0.668 mmole) of $(CH_3COO)_2Pd$ were dissolved in 25 ml of benzene. The resulting solution was refluxed for 72 hours. The reactant was washed with 400 ml of benzene until colorless and dried in a vacuum desiccator for 24 hours to produce a heterogenized palladium acetate catalyst.

EXAMPLE 12

A heterogenized palladium catalyst was prepared by following the procedure of Example 11 except that phosphinated 20% DVB-PS resin (0.98 g) and 0.15 g (0.668 mmole) of $(CH_3COO)_2Pd$ were dissolved in 25 ml of benzene.

PREPARATION OF ETHYLIDENE DIACETATE

The following examples 13–19 illustrate the preparation of ethylidene diacetate using catalysts in accord with the present invention.

EXAMPLE 13

30.03 g (0.4029 mmole) of methylacetate, 21.2 g (0,144 mmole) of iodomethane, 0.15 g of the catalyst $RhCl(CO)[P(C_6H_5)_3]_2/20\%$ DVB-PS resin prepared as in Example 8 and 2.46 g (0.026 mmole) of 3-picoline accelerator were charged into a reactor. The reactor was supplied with carbon monoxide and hydrogen and reacted with stirring at 150° C. and 70 atmospheres for 4 hours. The reactor was cooled to room temperature and the reaction products filtered to separate the produced ethylidene diacetate.

The products were analyzed by gas chromatography. The results of the gas chromatographic analysis of products are shown in Table 1.

TABLE 1

| Reaction temp (°C.) | Reaction pressure (atm) | Reaction time (hr) | Based on methyl acetate | | Conversion (%) |
|---|---|---|---|---|---|
| | | | Conversion (%) | Yield (%) | |
| 150 | 70 | 4 | 12.3 | 3.3 | 21.9 |

| Yield (%) | | | Selectivity (%) | | |
|---|---|---|---|---|---|
| ED* | Anhydrous acetic acid | Acetic acid | ED* | Anhydrous acetic acid | Acetic acid |
| 3.0 | 18.9 | 0 | 13.9 | 86.1 | 0 |

*Ed: Ethylidene diacetate

Example 14

The procedure of Example 13 was repeated except that the catalyst was changed to 0.15 g of $RhCl(CO)[P(C_6H_5)_3]_2/2\%$ DVB-PS resin catalyst prepared as in Example 4. The results of the gas chromatographic analysis of products are shown in Table 2.

TABLE 2

| Reaction | Reaction | Based on methyl acetate | | Con- |

TABLE 2-continued

| Reaction temp (°C.) | pressure (atm) | time (hr) | Conversion (%) | Yield (%) | version (%) |
|---|---|---|---|---|---|
| 150 | 70 | 4 | 45.8 | 5.8 | 22.7 |

| Yield (%) | | | Selectivity (%) | | |
|---|---|---|---|---|---|
| ED* | Anhydrous acetic acid | Acetic acid | ED* | Anhydrous acetic acid | Acetic acid |
| 8.3 | 14.4 | 0 | 36.5 | 63.5 | 0 |

*Ed: Ethylidene diacetate

EXAMPLE 15

The procedure of Example 13 was repeated except that the catalyst was changed to 0.15 g of $RhCl(CO)[P(C_6H_5)_3]_2$ /20% DVB-PS resin catalyst. The results of the gas chromatographic analysis of products are shown in Table 3.

TABLE 3

| Reaction temp (°C.) | Reaction pressure (atm) | Reaction time (hr) | Based on methyl acetate | | Conversion (%) |
|---|---|---|---|---|---|
| | | | Conversion (%) | Yield (%) | |
| 150 | 70 | 4 | 23.2 | 11.6 | 26.3 |

| Yield (%) | | | Selectivity (%) | | |
|---|---|---|---|---|---|
| ED* | Anhydrous acetic acid | Acetic acid | ED* | Anhydrous acetic acid | Acetic acid |
| 12.2 | 14.1 | 0 | 46.2 | 53.8 | 0 |

*Ed: Ethylidene diacetate

EXAMPLE 16

The procedure of Example 13 was repeated except the catalyst was changed to 0.15 g of $RhCl(CO)[P(C_6H_5)_3]_2$ /2% DVB-PS resin catalyst. The results of the gas chromatographic analysis of products are shown in Table 4.

TABLE 4

| Reaction temp (°C.) | Reaction pressure (atm) | Reaction time (hr) | Based on methyl acetate | | Conversion (%) |
|---|---|---|---|---|---|
| | | | Conversion (%) | Yield (%) | |
| 150 | 70 | 4 | 60.2 | 33.0 | 56.0 |

| Yield (%) | | | Selectivity (%) | | |
|---|---|---|---|---|---|
| ED* | Anhydrous acetic acid | Acetic acid | ED* | Anhydrous acetic acid | Acetic acid |
| 35.3 | 20.7 | 0 | 63.1 | 36.9 | 0 |

*Ed: Ethylidene diacetate

EXAMPLE 17

The procedure of Example 13 was repeated except that the catalyst was changed to 0.15 g of $(CH_3COO)_2Pd$ /20% DVB-PS resin catalyst as prepared in Example 12. The results of the gas chromatographic analysis of products are shown in Table 5.

TABLE 5

| Reaction temp (°C.) | Reaction pressure (atm) | Reaction time (hr) | Based on methyl acetate | | Conversion (%) |
|---|---|---|---|---|---|
| | | | Conversion (%) | Yield (%) | |
| 150 | 70 | 4 | 13.4 | 5.4 | 13.1 |

| Yield (%) | | | Selectivity (%) | | |
|---|---|---|---|---|---|
| ED* | Anhydrous acetic acid | Acetic acid | ED* | Anhydrous acetic acid | Acetic acid |
| 5.4 | 7.7 | 0 | 41.5 | 58.5 | 0 |

*Ed: Ethylidene diacetate

EXAMPLE 18

The procedure of Example 13 was repeated except that the catalyst was changed to 0.15 g of $(CH_3COO)_2Pd$ /20% DVB-PS resin catalyst as prepared in Example 12. The results of the gas chromatographic analysis of products are shown in Table 6.

TABLE 6

| Reaction temp (°C.) | Reaction pressure (atm) | Reaction time (hr) | Based on methyl acetate | | Conversion (%) |
|---|---|---|---|---|---|
| | | | Conversion (%) | Yield (%) | |
| 150 | 70 | 4 | 45.4 | 8.9 | 38.3 |

| Yield (%) | | | Selectivity (%) | | |
|---|---|---|---|---|---|
| ED* | Anhydrous acetic acid | Acetic acid | ED* | Anhydrous acetic acid | Acetic acid |
| 10.1 | 3.9 | 24.3 | 26.3 | 10.2 | 63.5 |

*Ed: Ethylidene diacetate

EXAMPLE 19

The procedure of Example 13 was repeated except that the catalyst was changed to 0.15 g of $(CH_3COO)_2Pd$ /2Pd/20% DVB-PS resin catalyst. The results of the gas chromatographic analysis of products are shown in Table 7.

TABLE 7

| Reaction temp (°C.) | Reaction pressure (atm) | Reaction time (hr) | Based on methyl acetate | | Conversion (%) |
|---|---|---|---|---|---|
| | | | Conversion (%) | Yield (%) | |
| 150 | 70 | 4 | 38.3 | 4.3 | 25.4 |

| Yield (%) | | | Selectivity (%) | | |
|---|---|---|---|---|---|
| ED* | Anhydrous acetic acid | Acetic acid | ED* | Anhydrous acetic acid | Acetic acid |
| 5.2 | 5.7 | 14.4 | 20.5 | 22.7 | 56.8 |

*Ed: Ethylidene diacetate

As shown in the results illustrated in Tables 1 to 17, the process of the present invention for producing ethylidene diacetate using a catalyst produced in accord with the present invention has several advantages. No by-product is formed. The purification of ethylidene diacetate is simplified because the catalyst is not mixed with the reaction product. Energy and time required for the process is reduced because complex separation procedures are not required. The process is simplified since no distillation step is required for purification of the product.

The foregoing description of the invention has been directed in primary part to a particular preferred embodiment and method in accordance with the requirements of the patent statutes and for purposes of explanation and illustration. It will be apparent, however, to those skilled in the art that many modifications and changes in the specifically described catalysts and methods may be made without departing from the scope and spirit of the invention. Therefore, the invention is not restricted to the particular catalysts and methods illustrated and described, but covers all modifications which may fall within the scope of the following claims.

It is Applicants' intention in the following claims to cover such modifications and variations as fall within the true spirit and scope of the invention.

What is claimed is:

1. A process for preparing ethylidene diacetate in a continuous reaction comprising reacting at a temperature between about 90°–250° C. and at a pressure between about 20–70 atmospheres, methyl acetate, iodomethane, carbon monoxide and hydrogen wherein the molar ratio of hydrogen to carbon monoxide is maintained between about 1:1 and about 6:1, said reaction occurring in the presence of an accelerator and a supported catalyst System represented by the formula $M_aX$ wherein, M is a compound of a group VIII transition metal which catalyzes the production of ethylidene diacetate;

X is an organic carrier; and

"a" represents the weight percent of said metal in said catalyst system.

2. The process of claim 1 wherein said metal is selected from the group consisting of rhodium and palladium.

3. The process of claim 2 wherein said compound M is selected from the group consisting of $RhCl(CO)[P(C_6H_5)_3]_2$, $RhCl(CO)[P(C_6H_5)_3]_3$, $(CH_3COO)_2Pd$ and $RhCl[P(C_6H_5)_3]_3$.

4. The process of claim 3 wherein said carrier X is selected from the group consisting of divinylbenzene-polystyrene copolymers.

5. The process of claim 4 wherein the degree of cross-linking of said copolymers is from about 1–20%.

6. The process of claim 5 wherein said weight percent of said metal is from about 0.1–2.0 weight percent.

7. The process of claim 1 wherein said accelerator is 3-picoline.

8. The process of claim 1 wherein said accelerator comprises about 1–10 wt. % of the total reactants.

9. The process of claim 1 wherein said iodomethane comprises about 20–70 wt. % of the total reactants.

10. The process of claim 1 wherein the molar ratio of hydrogen to carbon monoxide is between about 1:1 to about 3:1.

* * * * *